United States Patent
Kikuchi

(10) Patent No.: US 7,663,760 B2
(45) Date of Patent: Feb. 16, 2010

(54) METHOD FOR CALCULATING OPTICAL CONSTANTS AND SUBSTRATE PROCESSING SYSTEM

(75) Inventor: Toshihiko Kikuchi, Nirasaki (JP)

(73) Assignee: Tokyo Electron Limited, Tokyo (JP)

( * ) Notice: Subject to any disclaimer, the term of this patent is extended or adjusted under 35 U.S.C. 154(b) by 134 days.

(21) Appl. No.: 11/932,274

(22) Filed: Oct. 31, 2007

(65) Prior Publication Data

US 2008/0297801 A1 Dec. 4, 2008

Related U.S. Application Data

(60) Provisional application No. 60/888,445, filed on Feb. 6, 2007.

(30) Foreign Application Priority Data

Nov. 10, 2006 (JP) .............................. 2006-305845

(51) Int. Cl.
 *G01N 21/55* (2006.01)
(52) U.S. Cl. .................. 356/445; 356/237.4; 356/237.5
(58) Field of Classification Search ................ 356/445, 356/432, 328, 237.2–237.5, 239.3, 239.7, 356/601; 700/121; 250/557; 438/16, 692, 438/8
See application file for complete search history.

(56) References Cited

U.S. PATENT DOCUMENTS

2003/0086097 A1* 5/2003 Finarov ...................... 356/630

FOREIGN PATENT DOCUMENTS

| JP | 2002-260994 | 9/2002 |
| JP | 2005-033187 | 2/2005 |

* cited by examiner

*Primary Examiner*—Gregory J Toatley, Jr.
*Assistant Examiner*—Tri T Ton
(74) *Attorney, Agent, or Firm*—Oblon, Spivak, McClelland, Maier & Neustadt, L.L.P.

(57) ABSTRACT

An optical constant calculation method capable of calculating an accurate optical constant of an underlayer film to accurately identify a substrate surface structure. After each of films is layered on a wafer, there are measured the reflectivity of an oxide film under which an organic insulation film is formed and the reflectivity of an organic insulation film exposed after removal by plasma of the oxide film. Based on the measured reflectivities, the optical constant of the organic insulation film after being altered by heat treatment and the optical constant of the organic insulation film after being altered by plasma are calculated.

4 Claims, 10 Drawing Sheets

METHOD FOR CALCULATING OPTICAL CONSTANTS AND SUBSTRATE PROCESSING SYSTEM

BACKGROUND OF THE INVENTION

1. Field of the Invention

The present invention relates to an optical constant calculation method and a substrate processing system, and more particularly, to a method for calculating optical constants of a plurality of films layered on a substrate and a substrate processing system in which the method is implemented.

2. Description of the Related Art

With advancement of downsizing of semiconductor devices, a circuit pattern is required to be more finely formed on a surface of a wafer used for the fabrication of semiconductor devices. To form a fine circuit pattern on a wafer having a plurality of films layered thereon, a wafer surface structure (for example, a wafer surface structure comprised of etched films) must be identified during the semiconductor device fabrication.

To identify the surface structure of an etched wafer, there has been known a method for observing and photographing a cleaved cross-section of the wafer using an SEM (scanning electron microscope). However, this method has a drawback that the wafer must be cut (destroyed) along the cross section to be observed.

To nondestructively identify the surface structure of an etched wafer, methods have been developed in which the wafer surface structure is identified by scatterometry such as reflectometry, ellipsometry, or the like generally used for resist pattern evaluation or the like (see, for example, Japanese Laid-open Patent Publication No. 2002-260994).

In particular, the reflectometry (as scatterometry) nondestructively identifies the wafer surface structure using n-values (refractive indexes) and k-values (damping coefficients), which are optical constants representing the wafer surface structure. More specifically, optical constants (n-values and k-values) of films layered on a surface of each wafer are calculated in advance. These layered films include, for example, a nitride film, an organic insulation film (low-k film), an oxide film, an antireflection film (BRAC film), and a resist film. Next, using the calculated optical constants of the films, models are prepared and stored each of which optically represents, e.g., a groove shape (more generally, a surface structure) of one of the wafers which are different in groove shape. Then, the reflectivity of a surface of a wafer whose surface structure is to be identified is measured. By selecting a groove shape model corresponding to the measured reflectivity, the surface structure (groove shape) of the wafer is identified (see, for example, Japanese Laid-open Patent Publication No. 2005-33187).

With the scatterometry, the wafer surface structure cannot be identified with accuracy when the calculated optical constants of the films are not accurate. To obviate this, it is extremely important to accurately calculate the optical constants of the films.

In the conventional optical constant calculation method, the reflectivity or the like of each of films to be layered on a wafer surface is measured immediately after each film is formed, and the optical constant of each film is then calculated. For the calculation of the optical constant of the formed film, the optical constant of an underlayer film of the formed film is used. The optical constant of the underlayer film is generally calculated immediately after the underlayer film is formed.

However, during the layered film formation, the density of the underlayer film whose optical constant has already been calculated can sometimes be changed when heat treatment is performed for formation of an upper film. In general, the optical constant changes with a change in density. This indicates that the optical constant of the underlayer film used for the calculation of the optical constant of the upper film is made different from the real optical constant of the underlayer film, resulting in inaccuracy of the optical constant of the upper film, which is calculated using the already calculated optical constant of the underlayer film.

The underlayer film is altered when it is etched, so that the optical constant thereof can further be changed. In a case where the wafer surface structure including the etched underlayer film is identified by reflectometry, the optical constant of the underlayer film used for the calculation of the optical constant of the upper film differs from the real optical constant of the underlayer film. Therefore, the wafer surface structure identified using the already calculated optical constant of the underlayer film becomes inaccurate.

SUMMARY OF THE INVENTION

The present invention provides an optical constant calculation method capable of calculating an accurate optical constant of an underlayer film to thereby accurately identify a substrate surface structure, and a substrate processing system for implementing the optical constant calculation method.

According to a first aspect of the present invention, there is provided a method for calculating optical constants of a plurality of films layered on a substrate, wherein the optical constant of at least one underlayer film among the plurality of the films changes while the plurality of films are layered, comprising calculating the optical constant of an underlayer film of each of the plurality of films when each of the films is removed and the underlayer film is exposed after the plurality of films are layered.

With the optical constant calculation method according to the present invention, when each film is removed and an underlayer film of each film is exposed after the plurality of films are layered, the optical constant of the exposed underlayer film is calculated. As a result, the optical constant of the underlayer film whose optical constant changes during the layered film formation can be calculated after the change of the optical constant. Thus, an accurate optical constant of the underlayer film can be calculated, thereby making it possible to accurately identify the surface structure of the substrate.

The plurality of films can include a nitride film, an organic insulation film, an oxide film, an antireflection film, and a photoresist film, which are layered in this order, the photoresist film having an opening portion thereof through which a part of the antireflection film is exposed, and the method can comprise calculating in advance optical constants of a nitride film and an oxide film each formed as a single film on the substrate, measuring a first reflectivity of the photoresist film and a second reflectivity of the exposed part of the antireflection film after the plurality of films are layered, measuring a third reflectivity of the organic insulation film after the exposed part of the antireflection film and the oxide film are removed using a plasma, measuring a fourth reflectivity of the oxide film after the photoresist film and the antireflection film are removed, calculating the optical constant of the organic insulation film based on the fourth reflectivity and the calculated optical constants of the nitride film and the oxide film, calculating the optical constant of the organic insulation film based on the third reflectivity and the calculated optical constants of the nitride film and the organic insulation film, calculating the optical constant of the antireflection film based on the second reflectivity and the calculated optical constants of the nitride film, the oxide film, and the organic insulation film, and calculating the optical constant of the photoresist film based on the first reflectivity and the calculated optical constants of the nitride film, the oxide film, the organic insulation film, and the antireflection film.

With this optical constant calculation method, the optical constants of a nitride film and an oxide film are calculated in advance. After the plurality of films are layered, the first and second reflectivities are measured. After the exposed part of the antireflection film and the oxide film are removed by plasma, the third reflectivity is measured. After the photoresist film and the antireflection film are removed by plasma, the fourth reflectivity is measured. Based on the fourth reflectivity and the calculated optical constants of the nitride film and the oxide film, the optical constant of the organic insulation film is calculated. Based on the third reflectivity and the calculated optical constants of the nitride film and the organic insulation film, the optical constant of the organic insulation film is calculated. Based on the second reflectivity and the calculated optical constants of the nitride film, the oxide film, and the organic insulation film, the optical constant of the antireflection film is calculated. Based on the first reflectivity and the calculated optical constants of the nitride film, the oxide film, the organic insulation film, and the antireflection film, the optical constant of the photoresist film is calculated. Although the organic insulation film is altered by heat treatment or the like during the layered film formation, since the optical constant of the organic insulation film is calculated after the plurality of films are layered, the optical constant of the organic insulation film after being altered by heat treatment or the like can be calculated. Furthermore, although the organic insulation film is also altered when the exposed part of the antireflection film and the oxide film are removed by plasma, since the optical constant of the organic insulation film is calculated based on the third reflectivity and the like which are measured after the exposed part of the antireflection film and the oxide film are removed, the optical constant of the organic insulation film after being altered by plasma can be calculated. That is, an accurate optical constant of the organic insulation film after being altered due to heat treatment and plasma can be calculated, thereby making it possible to accurately identify the surface structure of the substrate.

Each of the optical constants can be a refractive index or a damping constant.

According to a second aspect of the present invention, there is provided a substrate processing system for processing a substrate having a plurality of films layered thereon, the plurality of films including at least one underlayer film whose optical constant changes while the plurality of films are layered, wherein the substrate processing system calculates the optical constant of an underlayer film of each of the plurality of films when each of the films is removed and the underlayer film is exposed after the plurality of films are layered.

The substrate processing system of this invention produces advantages that are the same or similar to those attained by the optical constant calculation method of this invention.

The substrate processing system can include a plasma processing apparatus adapted to remove each of the plurality of films on a surface of the substrate using plasma etching, and a reflectometry apparatus adapted to observe reflection light reflected from each of the plurality of films when light is projected onto the surface of the substrate, the plurality of films can include a nitride film, an organic insulation film, an oxide film, an antireflection film, and a photoresist film, which are layered in this order, the photoresist film having an opening portion thereof through which a part of the antireflection film is exposed, and the substrate processing system can be adapted to calculate in advance optical constants of a nitride film and an oxide film each formed as a single film on the substrate, measure a first reflectivity of the photoresist film and a second reflectivity of the exposed part of the antireflection film after the plurality of films are layered, measure a third reflectivity of the organic insulation film after the exposed part of the antireflection film and the oxide film are removed using a plasma, measure a fourth reflectivity of the oxide film after the photoresist film and the antireflection film are removed, calculate the optical constant of the organic insulation film based on the fourth reflectivity and the calculated optical constants of the nitride film and the oxide film, calculate the optical constant of the organic insulation film based on the third reflectivity and the calculated optical constants of the nitride film and the organic insulation film, calculate the optical constant of the antireflection film based on the second reflectivity and the calculated optical constants of the nitride film, the oxide film, and the organic insulation film, and calculate the optical constant of the photoresist film based on the first reflectivity and the calculated optical constants of the nitride film, the oxide film, the organic insulation film, and the antireflection film.

Each of the optical constants can be a refractive index or a damping constant.

Further features of the present invention will become apparent from the following description of an exemplary embodiment with reference to the attached drawings.

BRIEF DESCRIPTION OF THE DRAWINGS

FIGS. 4A to 4F are a process diagram for explaining an optical constant calculation method according to the embodiment, wherein FIG. 4A shows a step of calculating the optical constant of a silicon nitride film, FIG. 4B shows a step of calculating the optical constant of an oxide film, FIG. 4C shows a step of calculating the reflectivity of an antireflection film, FIG. 4D shows a step of calculating the reflectivity of an organic insulation film, FIG. 4E shows a step of calculating the reflectivity of the oxide film, and FIG. 4F shows a step of forming a trench in the organic insulation film;

DETAILED DESCRIPTION OF THE PREFERRED EMBODIMENT

The present invention will now be described in detail below with reference to the drawings showing a preferred embodiment thereof.

First, a substrate processing system according to one embodiment of the present invention will be explained.

Figure 1:
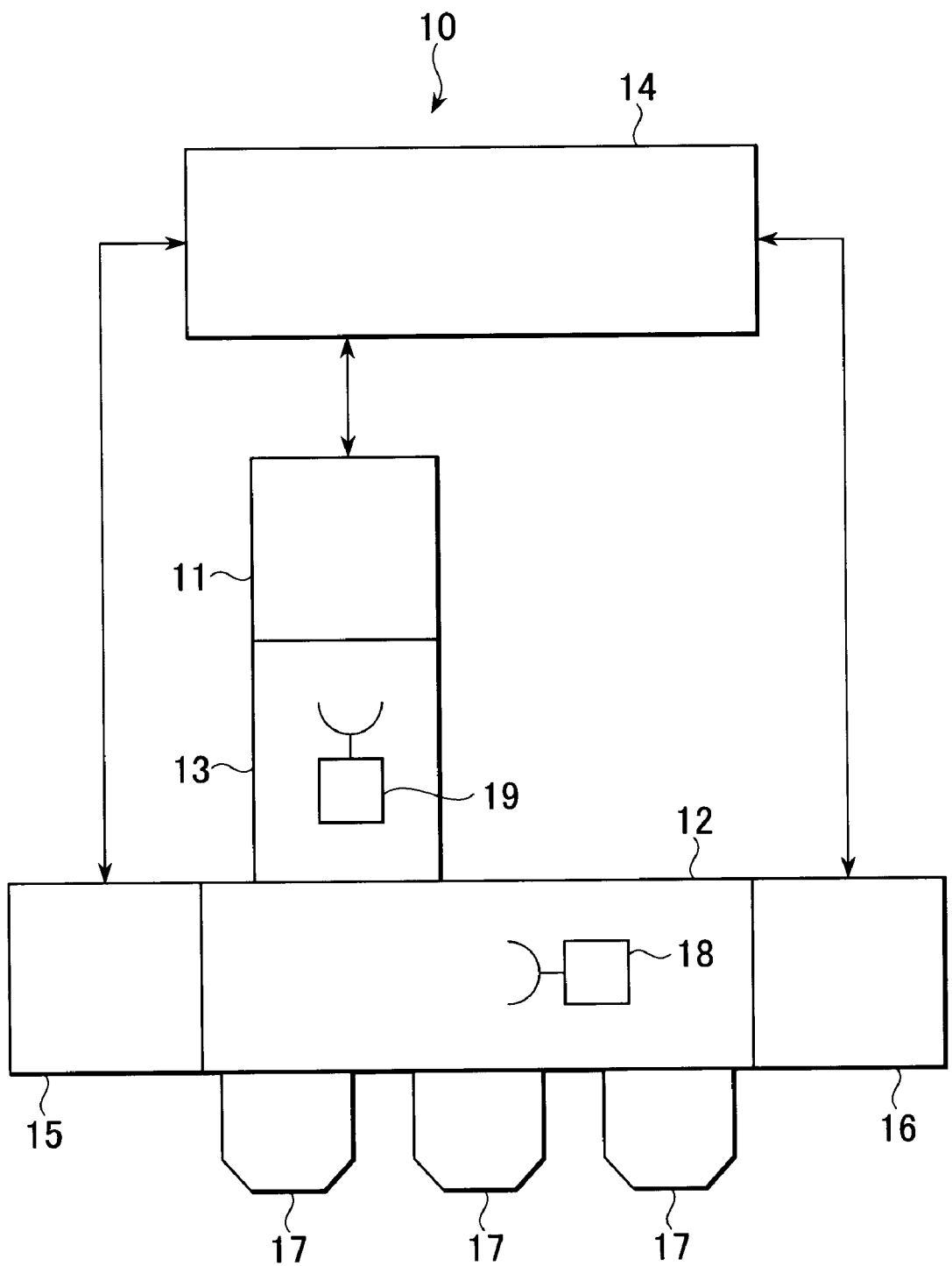
FIG. 1 is a plan view schematically showing the construction of a substrate processing system of one embodiment of the present invention.

FIG. 1 is a plan view schematically showing the construction of the substrate processing system of the embodiment.

As shown in FIG. 1, the substrate processing system 10 includes a process module 11 (plasma processing apparatus), a loader module 12, a load lock module 13 disposed between the process module 11 and the loader module 12 and connected thereto, and a system controller 14.

The process module 11 includes a decompression processing chamber, receives a semiconductor wafer (hereinafter referred to as the "wafer") W in the decompression processing chamber, and etches the wafer W.

The loader module 12, which is a chassis-like structure, has opposite ends thereof respectively provided with an orienter 15 and a metrology 16 (reflectometry apparatus), and has one side surface thereof provided with a plurality of load ports 17, the one side surface of the loader module 12 being opposite from another side surface thereof to which the load lock module 13 is connected. A wafer cassette adapted to receive a plurality of wafers W is disposed at each of the load ports 17. Inside the loader module 12, there is movably disposed a transfer arm mechanism 18 that can take a wafer W out of any of the wafer cassettes and can transfer the wafer W between the orienter 15, the load lock module 13, and the metrology 16. The orienter 15 can adjust the position of the wafer W having been transferred thereinto. The metrology 16 can observe reflection light from a surface of the wafer W having been transferred there. The construction and function of the metrology 16 will be described later.

The load lock module 13 is a transfer chamber in which is disposed a transfer arm mechanism 19 that can transfer a wafer W between the process module 11 and the loader module 12.

Figure 2:
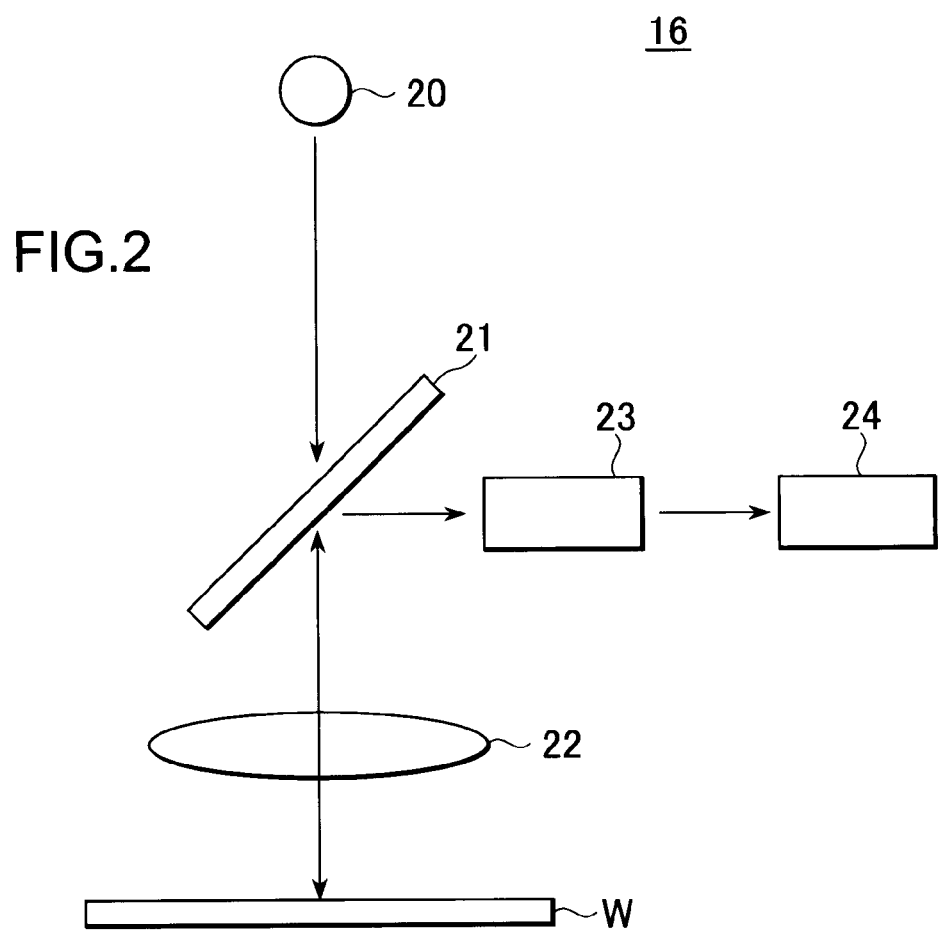
FIG. 2 is a view schematically showing the construction of a metrology shown in FIG. 1.

FIG. 2 is a view schematically showing the construction of the metrology 16 shown in FIG. 1. As shown in FIG. 2, the metrology 16 includes a light source 20, a half mirror 21, a collective lens 22, a spectrometer 23, and a detector 24. The light source 20, the half mirror 21, and the collective lens 22 are disposed on a straight line to face a wafer W. The half mirror 21, the spectrometer 23, and the detector 24 are disposed on another straight line.

The metrology 16 can observe reflection light from a surface of a wafer W. Specifically, white light irradiated from the light source 20 passes through the half mirror 21, is collected by the collective lens 22, and is incident on the wafer W. The incident white light is reflected by the surface of the wafer W. The reflection light from the surface of the wafer W is changed in its propagation path by the half mirror 21, passes through the spectrometer 23, and is incident on the detector 24. The detector 24 receives the incident reflection light, converts the reflection light into an electrical signal, and transmits the signal to the system controller 14.

Referring to FIG. 1 again, the system controller 14 can control operations of construction parts of the substrate processing system 10. The system controller 14 can identify a surface structure of a wafer W by reflectometry, which is scatterometry. The reflectometry is a shape identification method in which white light is irradiated onto a wafer, and a surface structure of the wafer W such as a CD (critical dimension) value of a groove (trench) is identified based on a ratio (reflectivity) between the intensity of incident light to the wafer W and the intensity of reflection light reflected by the wafer W.

Figure 3:
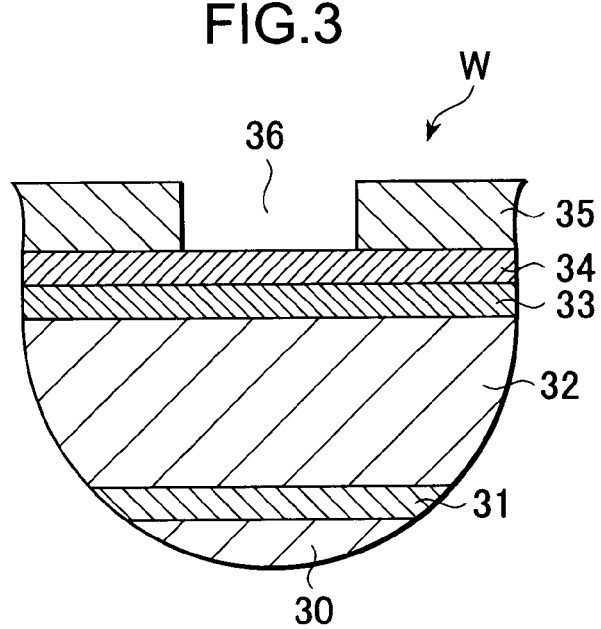
FIG. 3 is a section view schematically showing the construction of a wafer whose surface structure is to be identified.

FIG. 3 is a section view schematically showing the construction of a wafer whose surface structure is to be identified.

As shown in FIG. 3, the wafer W has a silicon substrate 30 on which a silicon nitride film 31, an organic insulation film 32, an oxide film 33, an antireflection film 34, and a photoresist film 35 are formed in layers in this order. The photoresist film 35 has an opening portion 36 formed therein. A part of the antireflection film 34 is exposed through the opening portion 36.

The wafer W is etched in the process module 11, whereby the antireflection film 34 and the photoresist film 35 are removed, and a trench 37 described below is formed in the organic insulation film 32.

The system controller 14 can calculate optical constants (each of which is an n value or a k value) of the films of the wafer W before the surface structure of the wafer W is identified by reflectometry. Specifically, reflectivities are calculated based on electrical signals each corresponding to the reflection light from each of the films and transmitted from the metrology 16. Then, the optical constants (each of which is an n value or a k value) of the silicon nitride film 31, the organic insulation film 32, the oxide film 33, the antireflection film 34, and the photoresist film 35 are calculated based on the calculated reflectivities.

Using the calculated optical constants of the films, the system controller 14 can prepare models each optically representing, e.g., one of trenches (more generally, surface structures) of wafers and store these models. The trenches are different in CD value from one another. Furthermore, the system controller 14 can calculate (measure) the reflectivity of a surface of a wafer W whose surface structure is to be identified, and then identify a CD value of a trench 37 of the wafer W by selecting a model representing a trench corresponding to the calculated reflectivity. Moreover, based on the identified CD value of the trench 37, the system controller 14 can modify the recipe of etching implemented in the process module 11.

It should be noted that the above described calculation of optical constants of the films and the identification of the shape of the trench can be carried out by a controller (not shown) provided in the metrology 16, other than the system controller 14. The surface structure of the wafer W to be identified by the system controller 14 may be the depth or inclination of the trench or thicknesses of the films other than the CD value of the trench.

In general, there are a variety of parameters used for the determination of optical constants. This requires that most of the parameters must be fixed for the calculation of the optical constants. To this end, the optical constant of one of the films is calculated at a time. Heretofore, the reflectivity of each film is measured immediately after the film is formed to be layered on the wafer surface, and the optical constant of the formed film is calculated based on the measured reflectivity of the formed film and the optical constants of underlayer films of the formed film. For example, the optical constant of the oxide film 33 is calculated based on the reflectivity of the oxide film 33 and the optical constants of the organic insulation film 32 and the silicon nitride film 31. The optical constant of the organic insulation film 32 is calculated immediately after the organic insulation film 32 is formed.

However, the organic insulation film 32 has its density that can change due to heat treatment for formation of the oxide film 33 on the organic insulation film 32 or due to plasma etching on the oxide film 33 or on the organic insulation film 32. With the change in the density, the optical constant of the organic insulation film 32 changes. Thus, the density of the organic insulation film 32 observed immediately after the formation of the organic insulation film 32 is different from that observed after the execution of the heat treatment on the oxide film 33 or the etching on the organic insulation film 32.

A conventional model that optically represents the trench 37 is prepared using the optical constant determined immediately after the formation of the organic insulation film 32. When the CD value of the trench 37 in the wafer W whose surface structure is to be identified is determined, the organic insulation film 32 is already altered due to heat treatment on the oxide film 33 or etching on the oxide film 33 or on the organic insulation film 32. Thus, the optical constant of the organic insulation film 32 used for the creation of the model differs from the real optical constant of the organic insulation film 32 at the time of identifying the CD value of the trench 37. As a result, the CD value of the trench 37 cannot accurately be identified, even if the model of the trench is selected which corresponds to the reflectivity having been measured for identification of the CD value of the trench 37.

Figure 4A:
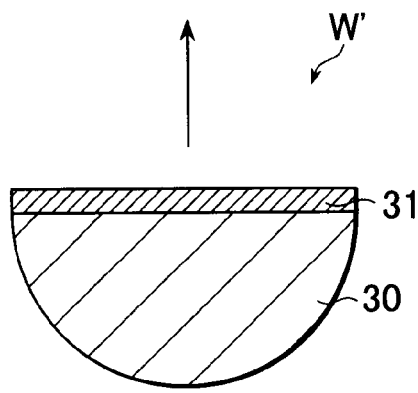
Figure 4B:
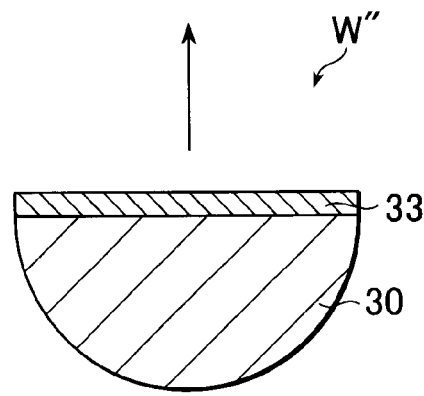

In view of the above, in the optical constant calculation method of this embodiment, the system controller 14 calculates the optical constant of each of the films of the wafer W when each film is removed by etching. More specifically, a wafer W' is prepared in advance in which a silicon nitride film 31 is formed as a single film on a silicon substrate 30, and a wafer W" is prepared in advance in which an oxide film 33 is formed as a single film on a silicon substrate 30. Then, the system controller 14 calculates the reflectivity of the silicon nitride film 31 of the wafer W', and based on the calculated reflectivity, calculates the optical constant of the silicon nitride film 31 (FIG. 4A). The system controller 14 further calculates the reflectivity of the oxide film 33 of the wafer W", and calculates the optical constant of the oxide film 33 (FIG. 4B) based on the calculated reflectivity.

Figure 4C:
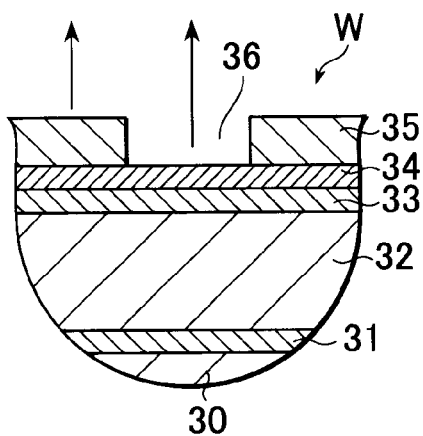
Figure 4D:
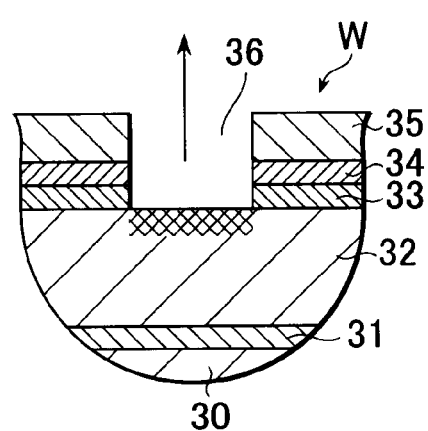

Furthermore, the system controller 14 calculates (measures) the reflectivity (first reflectivity) of the photoresist film 35 and the reflectivity (second reflectivity) of part of the antireflection film 34 exposed through the opening portion 36 in the wafer W having films layered thereon (FIG. 4C). Then, after the exposed part of the antireflection film 34 and the oxide film 33 formed thereunder are removed by plasma etching, the system controller 14 calculates (measures) the reflectivity (third reflectivity) of the exposed organic insulation film 32 (FIG. 4D). At that time, the exposed organic insulation film 32 is already altered due to plasma (as shown by hatching in FIG. 4D).

Figure 4E:
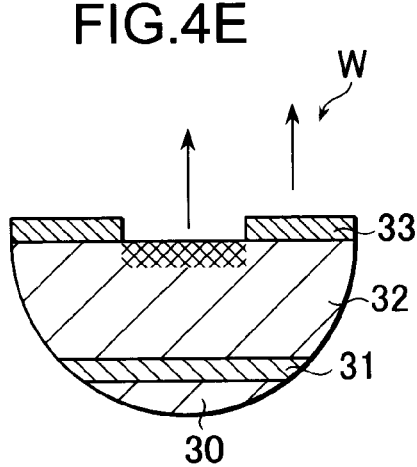

After the photoresist film 35 and the antireflection film 34 are removed by ashing, the system controller 14 calculates (measures) the reflectivity (fourth reflectivity) of the oxide film 33 (FIG. 4E).

Figure 4F:
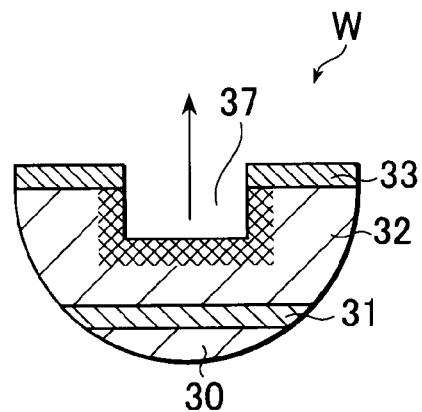

It should be noted that the reflectivity of the organic insulation film 32 altered by plasma can be calculated (measured) after removal by ashing of the photoresist film 35 and the antireflection film 34 (FIG. 4E). Alternatively, the reflectivity of the organic insulation film 32 can be calculated after the trench 37 is formed in the organic insulation film 32 by plasma etching (FIG. 4F).

Since the organic insulation film 32 and the silicon nitride film 31 are present under the oxide film 33 (FIG. 4E), the system controller 14 calculates the optical constant of the organic insulation film 32 based on the reflectivity of the oxide film 33 and the optical constants of the silicon nitride film 31 and the oxide film 33. At that time, since the organic insulation film 32 whose optical constant is to be calculated is covered by the oxide film 33, the organic insulation film 32 is not altered by plasma, but is altered by heat treatment on the oxide film 33 during the layered film formation. For this reason, the optical constant of the organic insulation film 32 after being altered by heat treatment is calculated.

Since the organic insulation film 32 and the silicon nitride film 31 after being altered by the heat treatment are present under the organic insulation film 32 altered by plasma (FIG. 4E), the system controller 14 calculates the optical constant of the organic insulation film 32 altered by plasma based on the reflectivity of the organic insulation film 32 altered by plasma, the optical constant of the silicon nitride film 31, and the optical constant of the organic insulation film 32 altered by the heat treatment.

Furthermore, since the oxide film 33, the organic insulation film 32 altered by the heat treatment, and the silicon nitride film 31 are present under the antireflection film 34 (FIG. 4C), the system controller 14 calculates the optical constant of the antireflection film 34 based on the reflectivity of part of the antireflection film 34, the optical constant of the silicon nitride film 31, the optical constant of the oxide film 33, and the optical constant of the organic insulation film 32 altered by heat treatment.

Since the antireflection film 34, the oxide film 33, the organic insulation film 32 altered by the heat treatment, and the silicon nitride film 31 are present under the photoresist film 35 (FIG. 4C), the system controller 14 calculates the optical constant of the photoresist film 35 based on the reflectivity of the photoresist film 35, the optical constant of the silicon nitride film 31, the optical constant of the oxide film 33, the optical constant of the organic insulation film 32 altered by the heat treatment, and the optical constant of the antireflection film 34.

With the optical constant calculation method according to the above described embodiment, the optical constant of the organic insulation film 32 altered by the heat treatment is calculated based on the reflectivity of the oxide film 33 measured after the removal of the photoresist film 35 and the antireflection film 34 from the wafer W formed with various films and based on the optical constants of the silicon nitride film 31 and the oxide film 33. Furthermore, the optical constant of the organic insulation film 32 altered by plasma is calculated based on the reflectivity of the organic insulation film 32 measured after the removal by etching of the exposed part of the antireflection film 34 and the oxide film 33 formed thereunder and based on the optical constant of the silicon nitride film 31 and the optical constant of the organic insulation film 32 altered by the heat treatment. Although the organic insulation film 32 is altered by the heat treatment when the films are layered, the optical constant of the organic insulation film 32 is calculated after the films are layered. Therefore, the optical constant of the organic insulation film 32 after being altered by the heat treatment can be calculated. Although the organic insulation film 32 are also altered by plasma when the exposed part of the antireflection film 34 and the oxide film 33 formed thereunder are removed by etching, the optical constant of the organic insulation film 32 is calculated based on the reflectivity of the organic insulation film 32 and the like measured after the removal by plasma of the exposed part of the antireflection film 34 and the oxide film 33. Therefore, the optical constant of the organic insulation film 32 after being altered by the plasma can be calculated, making it possible to accurately calculate the optical constant of the organic insulation film 32 after being altered by the heat treatment and plasma.

In the above described optical constant calculation method, since the optical constants of the antireflection film 34 and the photoresist film 35 are each calculated based on the optical constant of the organic insulation film 32 after being altered by the heat treatment and the like, the optical constants of the antireflection film 34 and the photoresist film 35 can be calculated with accuracy.

Furthermore, in the above described optical constant calculation method, the optical constants are calculated on the basis of the reflectivities of the various films, and therefore, it is unnecessary to cut the wafer W, making it possible to reduce costs.

Figure 5:
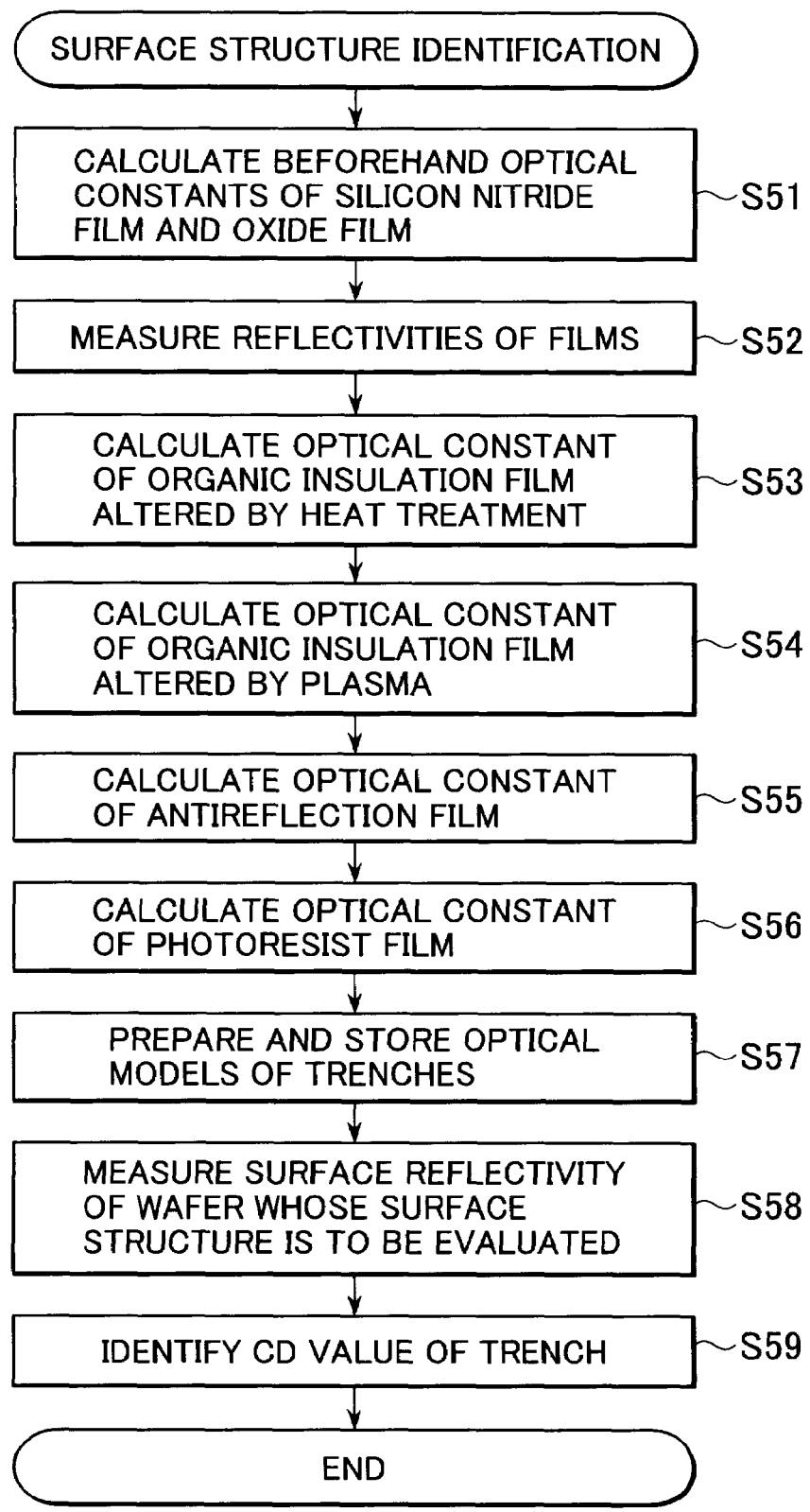
FIG. 5 is a flowchart of a process implemented by a system controller shown in FIG. 1 to identify a wafer surface structure.

FIG. 5 is a flowchart of a process for identifying a wafer surface structure, which is implemented by the system controller of FIG. 1.

As shown in FIG. 5, the optical constants of the silicon nitride film 31 and the oxide film 33 are calculated in advance respectively from the reflectivity of the silicon nitride film 31 of the wafer W' and the reflectivity of the oxide film 33 of the wafer W" (step S51). Next, for the wafer W used for optical constant calculation and having various films formed thereon, there are measured the reflectivity of the photoresist film 35, the reflectivity of the exposed part of the antireflection film 34, the reflectivity of the organic insulation film 32 exposed after removal by etching of the exposed part of the antireflection film 34 and the oxide film 33, and the reflectivity of the oxide film 33 exposed after removal by ashing of the photoresist film 35 and the antireflection film 34 (step S52).

Next, the optical constant of the organic insulation film 32 is calculated based on the reflectivity of the oxide film 33 and the optical constants of the silicon nitride film 31 and the oxide film 33 (step S53). At that time, the optical constant of the organic insulation film 32 after being altered by heat treatment can be calculated with accuracy.

Next, the optical constant of the organic insulation film 32 altered by plasma is calculated based on the reflectivity of the organic insulation film 32 altered by plasma, the optical constant of the silicon nitride film 31, and the optical constant of the organic insulation film 32 altered by heat treatment (step S54). As a result, the optical constant of the organic insulation film 32 after being altered by plasma can be accurately calculated.

Next, the optical constant of the antireflection film 34 is calculated based on the reflectivity of part of the antireflection film 34, the optical constant of the silicon nitride film 31, the optical constant of the oxide film 33, and the optical constant of the organic insulation film 32 altered by heat treatment (step S55). Then, the optical constant of the photoresist film 35 is calculated based on the reflectivity of the photoresist film 35, the optical constant of the silicon nitride film 31, the optical constant of the oxide film 33, the optical constant of the organic insulation film 32 altered by the heat treatment, and the optical constant of the antireflection film 34 (step S56). As a result, accurate optical constants of the antireflection film 34 and the photoresist film 35 can be calculated.

Next, using the calculated optical constants of the various films, there are prepared and stored models each optically representing one of trenches which are different in CD value from one another (step S57).

Next, a surface reflectivity of the wafer W whose surface structure is to be identified is measured (step S58), and the CD value of the trench 37 is identified by selecting a model of a trench corresponding to the measured reflectivity (step S59).

With the process shown in FIG. 5, models optically representing trenches are prepared using accurate optical constants of the various films, and one of the prepared models is selected to identify the CD value of the trench 37. As a result, an accurate CD value can be identified.

To identify the CD values of trenches 37 respectively formed in a plurality of wafers W, it is enough to carry out all the steps of the process of FIG. 5 only for a first wafer W and carry out only steps S58 and S59 of the process for the remaining wafers W. When there are excess wafers W, wafers W used for calculation of optical constants of various films are prepared, and steps S51 to S57 in the process of FIG. 5 may be implemented on these wafers W.

In the above described substrate processing system 10, the metrology 16 is configured to have the half mirror 21. However, the construction of the metrology 16 is not limited thereto.

Figure 6:
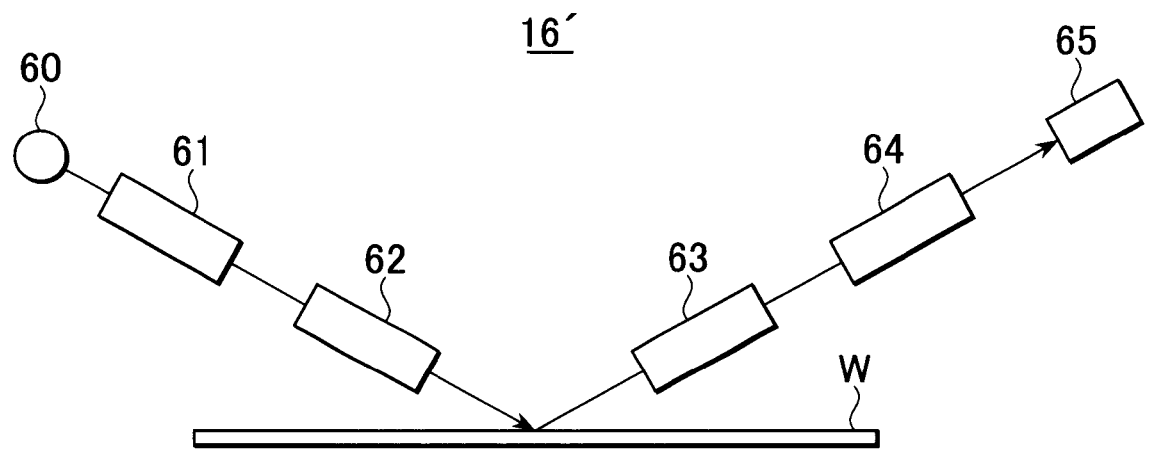
FIG. 6 is a view schematically showing the construction of a modification of the metrology shown in FIG. 1.

FIG. 6 is a view schematically showing the construction of a modification of the metrology shown in FIG. 1.

As shown in FIG. 6, a metrology 16' is comprised of a light source 60, a polarizer 61, a compensator 62, an analyzer 63, a spectroscope 64, and a detector 65. The light source 60, the polarizer 61, and the compensator 62 are arranged on a straight line extending at a predetermined angle of attack with respect to the surface of the wafer W. The analyzer 63, the spectroscope 64, and the detector 65 are arranged on another straight line so as to be respectively symmetrical with the light source 60, the polarizer 61, and the compensator 62 with respect to an axis normal to the wafer W.

The metrology 16' can observe reflection light from a surface of a wafer W. Specifically, white light irradiated from the light source 60 passes through the polarizer 61 and the compensator 62, and is incident on the wafer W. The incident white light is reflected by the surface of the wafer W. The reflection light from the surface of the wafer W is incident on the detector 65 through the analyzer 63 and the spectroscope 64. The detector 65 receives the incident reflection light, converts the reflection light into an electrical signal, and transmits the electrical signal to the system controller 14.

In the above described substrate processing system 10, the metrology 16 is connected to the loader module 12. Alternatively, however, the metrology 16 can be separated from the loader module 12 and can be disposed at a location different from the substrate processing system 10.

In the above described surface structure identification process of FIG. 5, the reflectometry is employed as scatterometry. However, the scatterometry can be of any type capable of identifying a surface structure based on the phase, intensity, or the like of reflection light obtained by irradiating white light onto the wafer W. For example, ellipsometry can be used.

The optical constant calculation method of this embodiment can be applied to any wafer having a film altered after being layered, other than the wafer W. Also in that case, an accurate optical constant of the altered film can be calculated.

It is to be understood that the present invention may also be accomplished by supplying to a computer or an external server a storage medium in which is stored a program code of software that realizes the functions of the above described embodiment, and then causing a CPU of the computer or the like to read out and execute the program code stored in the storage medium.

In this case, the program code itself read out from the storage medium realizes the functions of the embodiment, and hence the program code and the storage medium in which the program code is stored constitute the present invention.

The storage medium for supplying the program code may be, for example, a RAM, an NV-RAM, a floppy (registered trademark) disk, a hard disk, a magnetic-optical disk, an optical disk such as a CD-ROM, a CD-R, a CD-RW, a DVD (DVD-ROM, DVD-RAM, DVD-RW, or DVD+RW), a magnetic tape, a non-volatile memory card, or a ROM. Alternatively, the program may be supplied to the computer or the like by being downloaded via a network from another computer, a database, or the like, not shown, connected to the Internet, a commercial network, a local area network, or the like.

Moreover, it is to be understood that the functions of the embodiment can be accomplished not only by executing a program code read out by the computer or the like, but also by causing an OS (operating system) or the like which operates on the CPU to perform a part or all of the actual operations based on instructions of the program code.

Furthermore, it is to be understood that the functions of the embodiment can also be accomplished by writing a program code read out from a storage medium into a memory provided on an expansion board inserted into the computer or in an expansion unit connected to the computer and then causing a CPU or the like provided on the expansion board or in the expansion unit to perform a part or all of the actual operations based on instructions of the program code.

The form of the program code may be an object code, a program code executed by an interpreter, script data supplied to an OS, or the like.

Next, a working example of this invention will be described specifically.

Working Example

First, step S51 was implemented to calculate the optical constants of the silicon nitride film 31 and the oxide film 33. Then, the reflectivity of the organic insulation film 32 was measured when the film 32 was formed and layered on the wafer W, and the optical constant of the organic insulation film 32 after being formed was calculated at different wavelengths based on the reflectivity of the organic insulation film 32 and the optical constant of the silicon nitride film 31. Graphs of FIGS. 7 and 8 respectively show calculated n-values (refractive indexes) and calculated k-values (damping coefficients), which correspond to lines "i" shown in FIGS. 7 and 8

Next, step S53 was implemented to calculate at different wavelengths the optical constant of the organic insulation film 32 after being altered by heat treatment. Calculated n-values and k-values (corresponding to lines "ii" in FIGS. 7 and 8) are respectively shown in the graphs in FIGS. 7 and 8.

Furthermore, step S54 was implemented to calculate the optical constant of the organic insulation film 32 after being altered by plasma. Calculated n-values and k-values are respectively shown in the graphs of FIGS. 7 and 8 (corresponding to lines "iii" in these figures).

Figure 7:
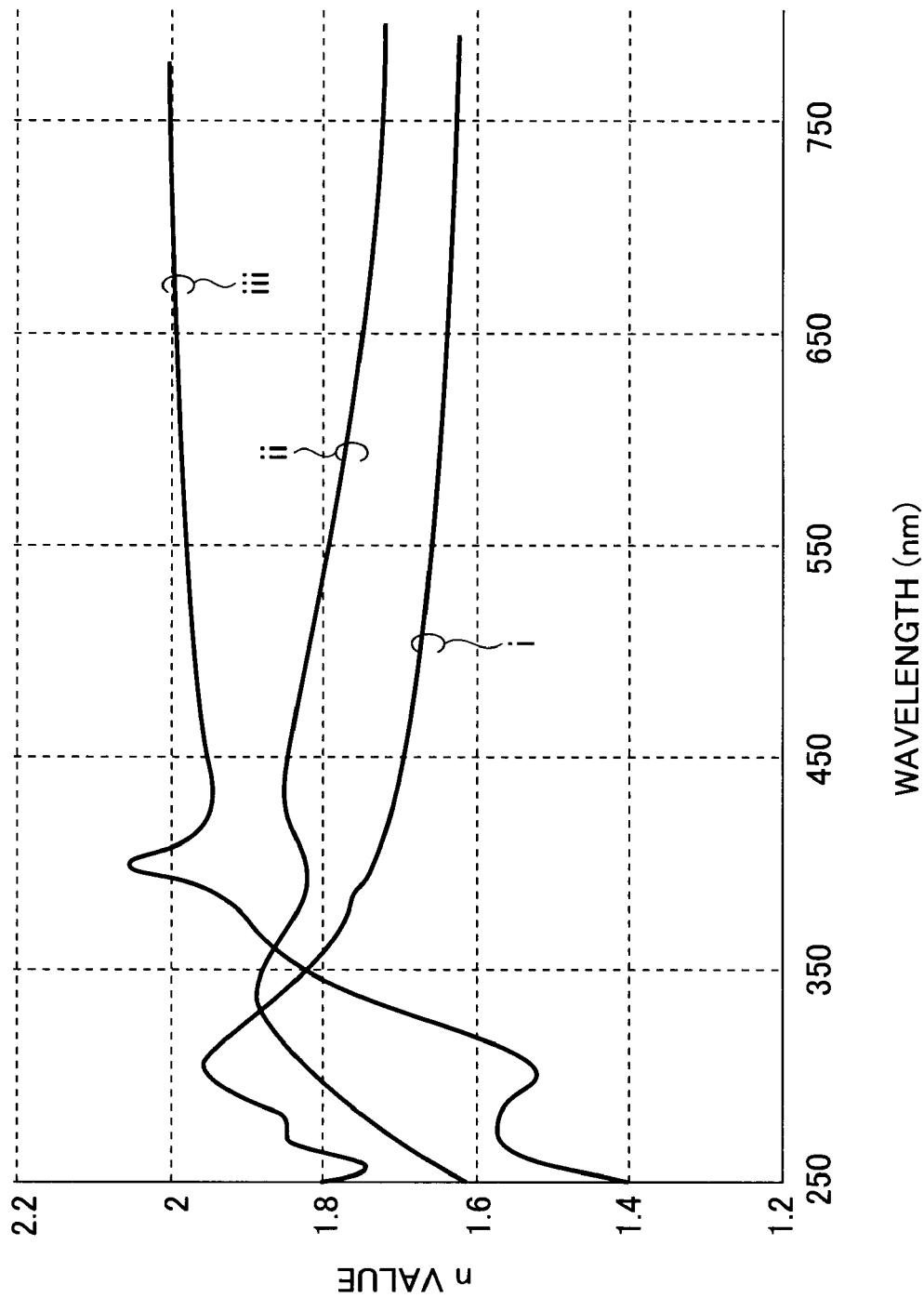
FIG. 7 is a graph showing calculated n-values of an organic insulation film as a function of wavelength.
Figure 8:
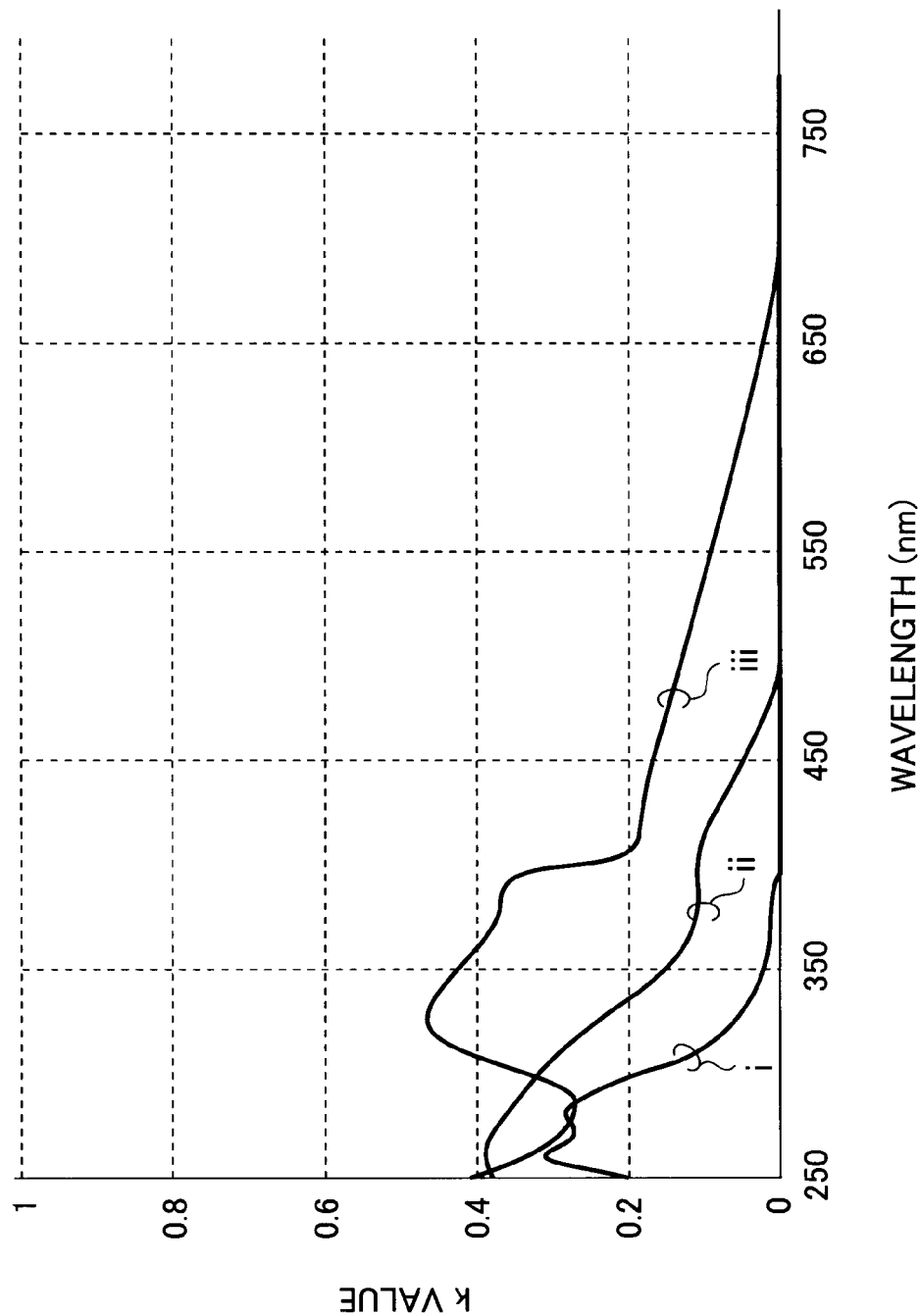
FIG. 8 is a graph showing calculated k-values of the organic insulation film as a function of wavelength.

From the graphs of FIGS. 7 and 8, it was confirmed that the optical constant of the organic insulation film 32 changed due to heat treatment and plasma processing.

Figure 9:
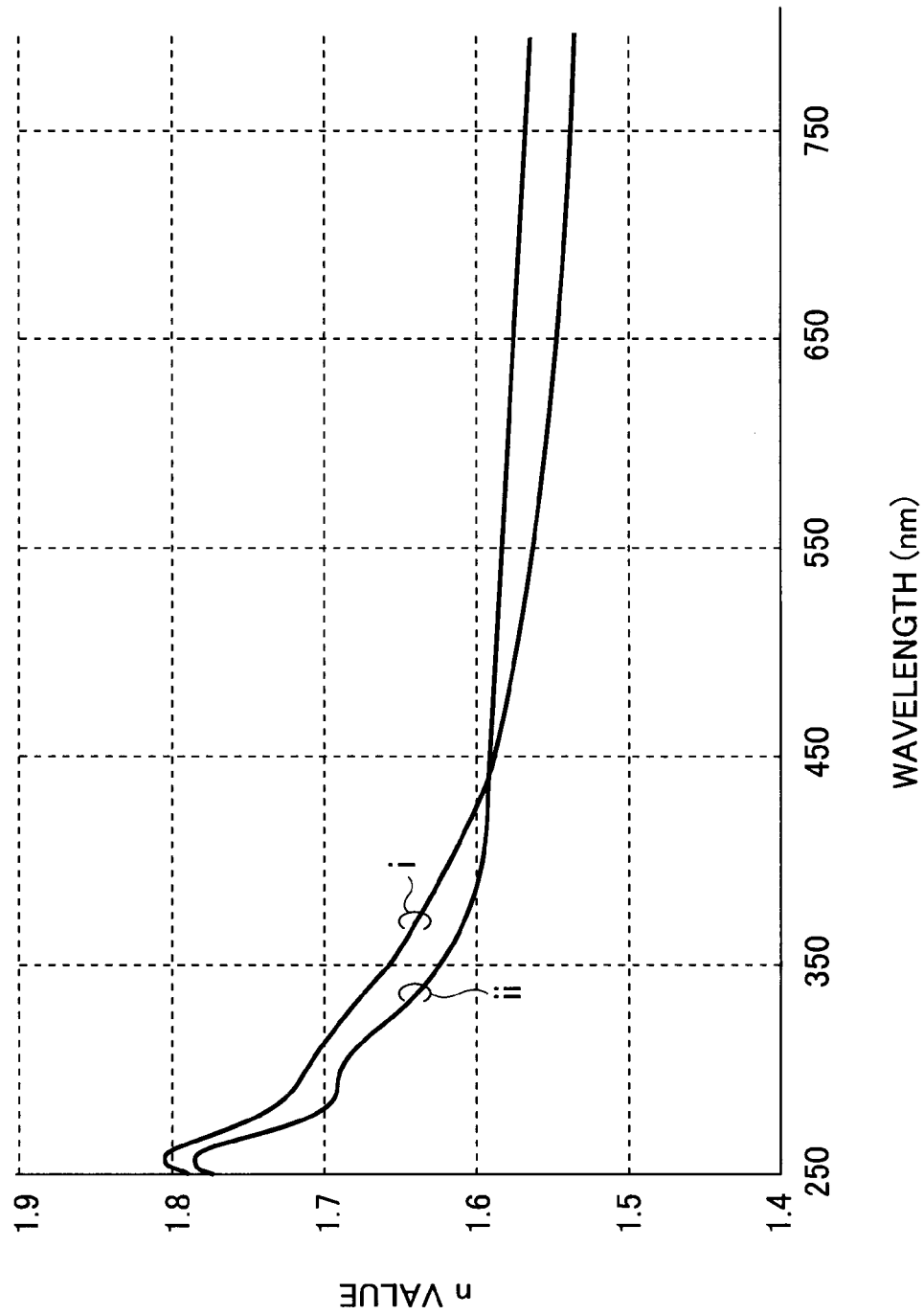
FIG. 9 is a graph showing calculated n-values of an antireflection film as a function of wavelength.
Figure 10:
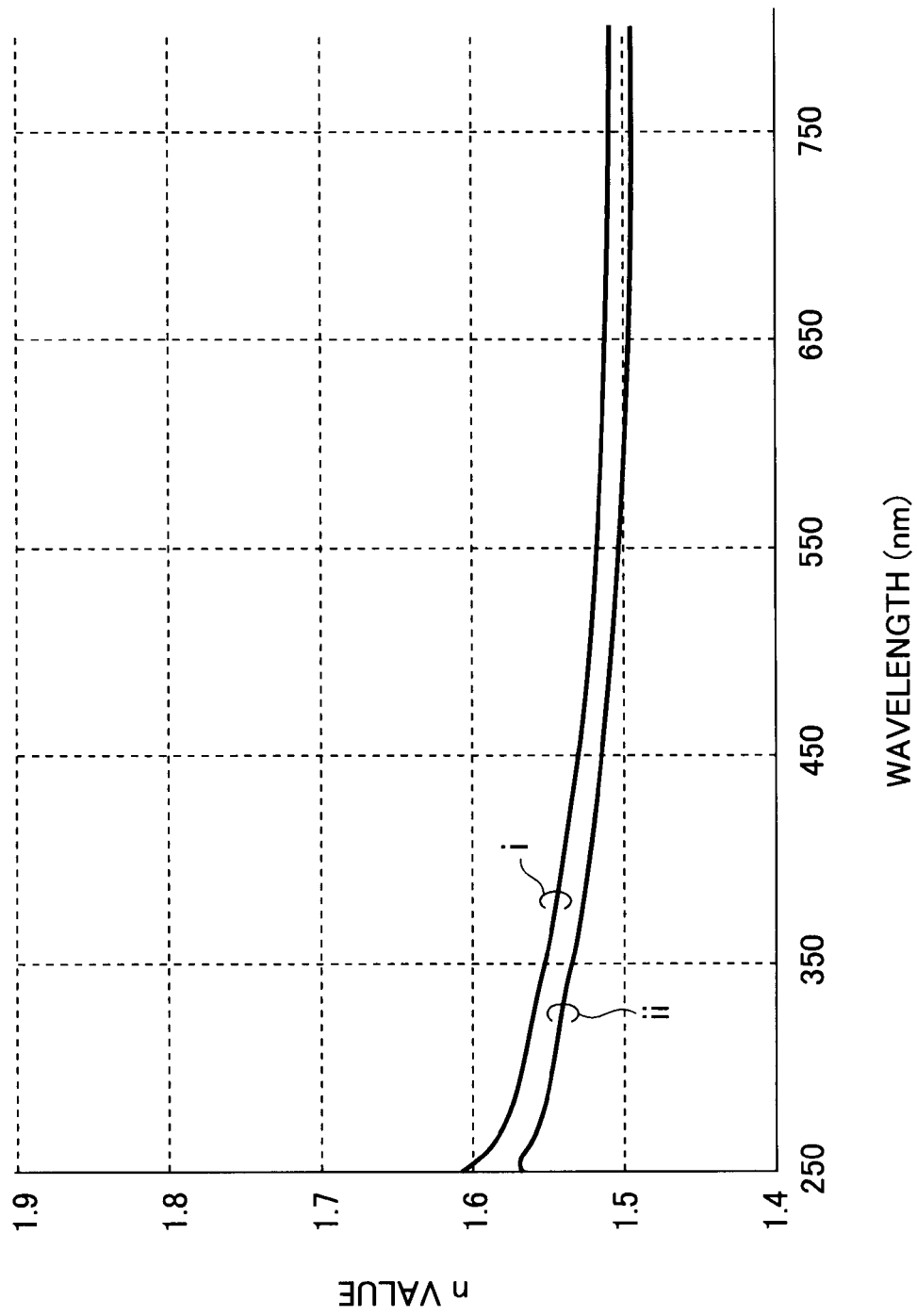
FIG. 10 is a graph showing n-values of a photoresist film as a function of wavelength.

Then, step S55 was implemented to calculate the optical constant of the antireflection film 34 at different wavelengths. Calculated n-values are shown in the graph of FIG. 9 (corresponding to a line "i" in the figure). Step S56 was implemented to calculate the optical constant of the photoresist film 35 at different wavelengths. Calculated n-values are shown in the graph of FIG. 10 (corresponding to a line "i" in the figure).

Figure 11:
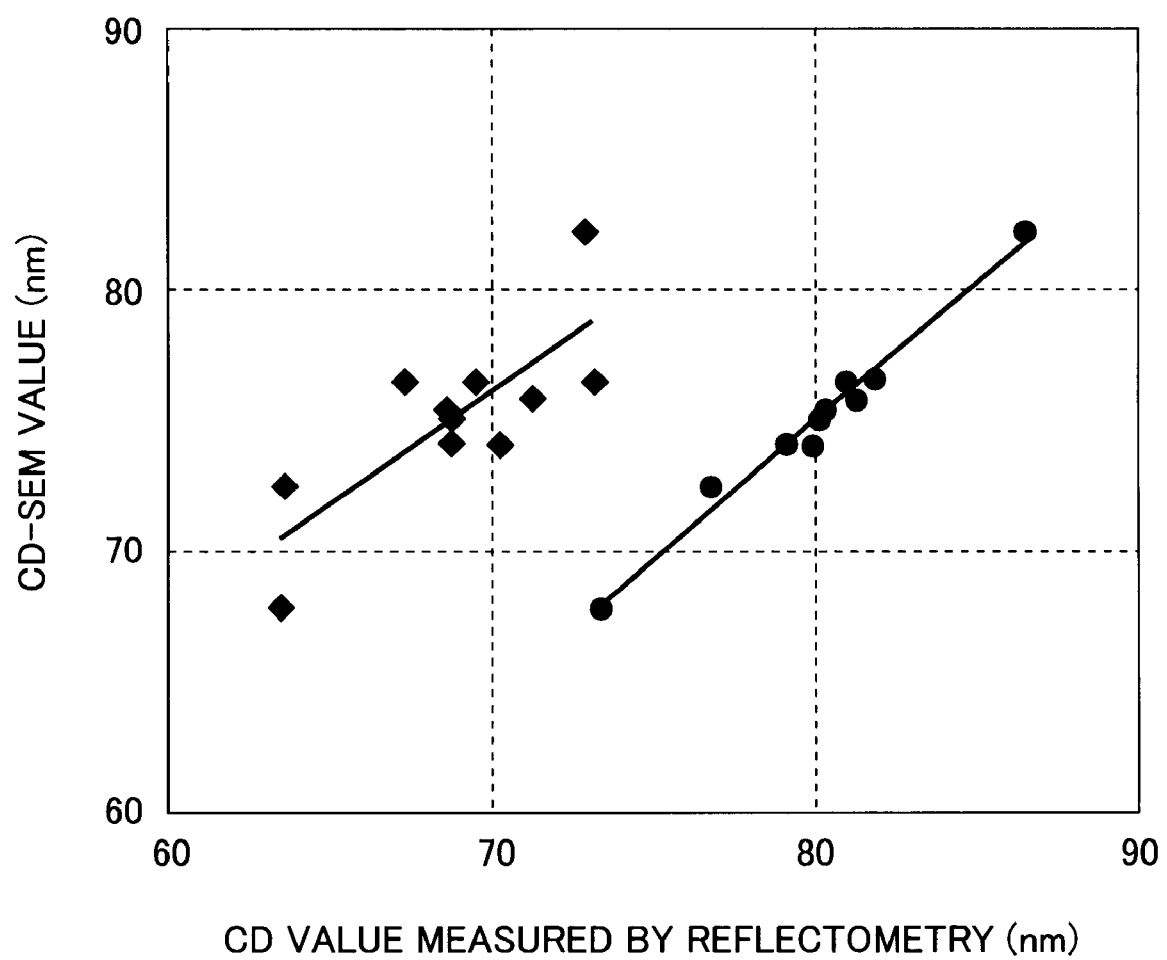
FIG. 11 is a graph showing a relation between CD values measured by reflectometry and CD-SEM values.

Next, steps S57 and S58 were implemented. Furthermore, steps S58 and S59 were implemented on a plurality of wafers W each having a surface structure to be identified, to thereby identify the CD value of a trench formed in each wafer. The CD values of the trenches of the wafers W each having the CD value identified by reflectometry were measured by SEM (hereinafter referred to as the CD-SEM values). A relation between the CD values measured by reflectometry and the CD-SEM values is shown in FIG. 11 in which the CD values measured by reflectometry and the CD-SEM values are plotted by black circle marks.

Comparison Example

During layered film fabrication on a wafer W, the reflectivity of each of a silicon nitride film 31, an organic insulation film 32, an oxide film 33, an antireflection film 34, and a photoresist film 35 was measured immediately after each film was formed. Using the measured reflectivities, the optical constant of each film after being formed was calculated at different wavelengths. Calculated n-values of the antireflection film 34 are shown in the graph of FIG. 9 (corresponding to a line "ii" in the figure), and calculated n-values of the photoresist film 35 are shown in the graph of FIG. 10 (corresponding to a line "ii" in the figure).

From the graphs of FIGS. 9 and 10, it was understood that the n-values and k-values of the working example differ from those of the comparison example. The reason why there were differences between the working example and the comparison example was considered as follows: In the working example, the optical constants of the antireflection film 34 and the photoresist film 35 were calculated based on the optical constant of the organic insulation film 32 after being altered by heat treatment. On the other hand, in the comparison example, the optical constants of the antireflection film 34 and the photoresist film 35 were calculated based on the optical constant of the organic insulation film 32 determined immediately after the film 32 was formed.

Next, models each optically representing one of trenches having different CD values were prepared and stored using the optical constants of the films each measured immediately after the formation of the film concerned. Then, the surface reflectivities of a plurality of wafers W each having a surface structure to be identified were measured. By selecting a trench model corresponding to each of the measured reflectivities (reflectometry), the CD value of the trench of each wafer W was identified. Furthermore, the CD-SEM values were measured for the wafers W whose CD values were identified by the reflectometry. That is, the CD values of the trenches of the wafers W were measured by SEM. A relation between the CD values determined by the reflectometry and the CD-SEM values are shown in FIG. 11 in which the CD values determined by the reflectometry and the CD-SEM values are plotted by black rhombus marks in FIG. 11.

As shown in the graph of FIG. 11, the standard error of a regression line of the CD values and the CD-SEM values is 1.65 nm in the working example, whereas the standard error is 6.79 nm in the comparison example. This indicates that the CD values in the working example are closer to the real CD values. In other words, it is understood that accurate optical constants of the films can be calculated using the optical constant calculation method of this invention, and as a result, accurate CD values can be identified.

What is claimed is:

1. A method for calculating optical constants of a plurality of films layered on a substrate, wherein the optical constant of at least one underlayer film among the plurality of the films changes while the plurality of films are layered, comprising:

calculating the optical constant of an underlayer film of each of the plurality of films when said each of the films is removed and said underlayer film is exposed after the plurality of films are layered;

wherein the plurality of films include a nitride film, an organic insulation film, an oxide film, an antireflection film, and a photoresist film, which are layered in this order, the photoresist film having an opening portion thereof through which a part of the antireflection film is exposed, and wherein the method further comprises:

calculating in advance optical constants of a nitride film and an oxide film each formed as a single film on the substrate;

measuring a first reflectivity of the photoresist film and a second reflectivity of the exposed part of the antireflection film after the plurality of films are layered;

measuring a third reflectivity of the organic insulation film after the exposed part of the antireflection film and the oxide film are removed using a plasma;

measuring a fourth reflectivity of the oxide film after the photoresist film and the antireflection film are removed;

calculating the optical constant of the organic insulation film based on the fourth reflectivity and the calculated optical constants of the nitride film and the oxide film;

calculating the optical constant of the organic insulation film based on the third reflectivity and the calculated optical constants of the nitride film and the organic insulation film;

calculating the optical constant of the antireflection film based on the second reflectivity and the calculated optical constants of the nitride film, the oxide film, and the organic insulation film; and calculating with a substrate processing system the optical constant of the photoresist film based on the first reflectivity and the calculated optical constants of the nitride film, the oxide film, the organic insulation film, and the antireflection film.

2. The method according to claim 1, wherein each of the optical constants is a refractive index or a damping constant.

3. A substrate processing system for processing a substrate having a plurality of films layered thereon, the plurality of films including at least one underlayer film whose optical constant changes while the plurality of films are layered, wherein the substrate processing system calculates the optical constant of an underlayer film of each of the plurality of films when said each of the films is removed and said underlayer film is exposed after the plurality of films are layered, and wherein the substrate processing system includes:

a plasma processing apparatus adapted to remove each of the plurality of films on a surface of the substrate using plasma etching; and a reflectometry apparatus adapted to observe reflection light reflected from each of the plurality of films when light is projected onto the surface of the substrate, wherein the plurality of films include a nitride film, an organic insulation film, an oxide film, an antireflection film, and a photoresist film, which are layered in this order, the photoresist film having an opening portion thereof through which a part of the antireflection film is exposed, and wherein the substrate processing system is adapted to:

calculate in advance optical constants of a nitride film and an oxide film each formed as a single film on the substrate;

measure first reflectivity of the photoresist film and a second reflectivity of the exposed part of the antireflection film after the plurality of films are layered;

measure a third reflectivity of the organic insulation film after the exposed part of the antireflection film and the oxide film are removed using a plasma;

measure a fourth reflectivity of the oxide film after the photoresist film and the antireflection film are removed;

calculate the optical constant of the organic insulation film based on the fourth reflectivity and the calculated optical constants of the nitride film and the oxide film;

calculate the optical constant of the organic insulation film based on the third reflectivity and the calculated optical constants of the nitride film and the organic insulation film;

calculate the optical constant of the antireflection film based on the second reflectivity and the calculated optical constants of the nitride film, the oxide film, and the organic insulation film; and calculated the optical constant of the photoresist film based on the first reflectivity and the calculated optical constants of the nitride film, the oxide film, the organic insulation film, and the antireflection film.

4. The substrate processing system according to claim 3, wherein each of the optical constants is a refractive index or a damping constant.

* * * * *